(12) United States Patent
Gupta

(10) Patent No.: US 6,264,800 B1
(45) Date of Patent: *Jul. 24, 2001

(54) PURIFICATION PROCESS

(75) Inventor: Vijai P. Gupta, Berwyn, PA (US)

(73) Assignee: Arco Chemical Technology, L.P., Greenville, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/619,157

(22) Filed: Jul. 19, 2000

(51) Int. Cl.[7] .............................. B01D 3/38; C07C 27/28; C07C 41/42

(52) U.S. Cl. .............................. 203/96; 203/97; 203/98; 203/100; 568/699; 568/868; 568/913

(58) Field of Search ...................... 203/91, 92, 93, 203/94, 95, 96, 97, 98, DIG. 25, 100; 568/913, 699, 868

(56) References Cited

U.S. PATENT DOCUMENTS

| | | | |
|---|---|---|---|
| 2,559,519 | * 7/1951 | Smith, Jr. et al. | 203/64 |
| 3,418,338 | * 12/1968 | Gilman et al. | 203/75 |
| 3,972,948 | * 8/1976 | Laemmle et al. | 568/618 |
| 4,359,365 | * 11/1982 | Deguchi et al. | 203/96 |
| 4,695,349 | * 9/1987 | Becker et al. | 203/96 |
| 5,395,982 | * 3/1995 | Cossata et al. | 568/699 |
| 5,552,024 | 9/1996 | Chang et al. | 203/78 |

FOREIGN PATENT DOCUMENTS

1180822  * 2/1970 (GB) .......................................... 2/2

* cited by examiner

Primary Examiner—Virginia Manoharan
(74) Attorney, Agent, or Firm—William C. Long

(57) ABSTRACT

A procedure is provided for the separation of close boiling impurities from products which have slightly higher polarity than the impurities, for example, separation of di-propylene glycol di-tert-butyl ether (DE) from di-propylene glycol mono-tert-butyl ether (DPTB) by distillation, water or steam being used as stripping component with heat provided by a reboiler.

3 Claims, 1 Drawing Sheet

PURIFICATION PROCESS

RELATED APPLICATIONS

This case is related to U.S. Ser. No. 09/283,110 filed Mar. 31, 1999.

BACKGROUND OF THE INVENTION

1. Field of the Invention

The present invention relates to the separation of glycol di-alkyl ethers from the corresponding mono-ethers, especially to the preparation of high purity di-propylene glycol mono-tert-butyl ether (DPTB) by the separation of impurities such as di-propylene glycol di-tert-butyl ether (DE) from the DPTB.

2. Description of the Prior Art

Di-propylene glycol mono-tert-butyl ether (DPTB) is used commercially as a solvent and, in combination with dipropylene glycol as a concrete additive.

A commercial process for the production of DPTB involves reacting di-propylene glycol (DPG) with isobutylene over an acid ion exchange resin catalyst. A problem with such procedures is that certain amounts of di-propylene glycol di-tert-butyl ether are also produced which must be separated from DPTB prior to use of the DPTB as a concrete additive since the di-ether has a pronounced adverse effect in the usage in concrete.

Currently a costly and tedious extractive distillation technology involving the use of two columns and very large recycle streams is employed to accomplish the separation; see U.S. Pat. No. 5,552,024.

Various methods are known for separating minor amounts of impurities from various products including azeotropic and extractive distillation procedures but such prior methods are generally complicated and expensive. Steam stripping techniques have been employed but tend to result in the introduction of unwanted impurities with the steam, as well as producing waste water from condensing steam.

Now, in accordance with the present invention there is provided a simple and effective distillation procedure whereby the separation of impurities such as the di-ether from DPTB is achieved.

BRIEF DESCRIPTION

In accordance with the invention, the DPTB to be purified is fed to the upper section of a fractional distillation column, while a stripping component comprised of liquid water or steam is fed to the column preferably at a point below the point of introduction of the mixture to be purified. It is important that DPG also be fed to the column, usually in admixture with the DPTB. The water or steam stream may be introduced into the bottom of the column as a preferred practice although this steam can be introduced at any point. A reboiler is provided wherein bottoms from the column is vaporized and circulated to the column thus providing heat to the column. Heat input into the column via the reboiler is sufficient to ensure vaporization of the liquid water stripping component stream introduced to the column, and the pressure maintained in the column is effective to prevent overheating especially in the reboiler, while maintaining stripping vapor flow upwardly through the column. The stripping component, e.g. water, with some DPTB plus undesirable di-ether impurities as well as unreacted isobutylene is removed overhead, DPTB product substantially reduced in di-ether is removed as bottoms in admixture with DPG. A portion or all of the water phase from the overhead condensate can be returned to the column as stripping water.

BRIEF DESCRIPTION OF THE DRAWINGS

The attached

DETAILED DESCRIPTION

Figure 1:
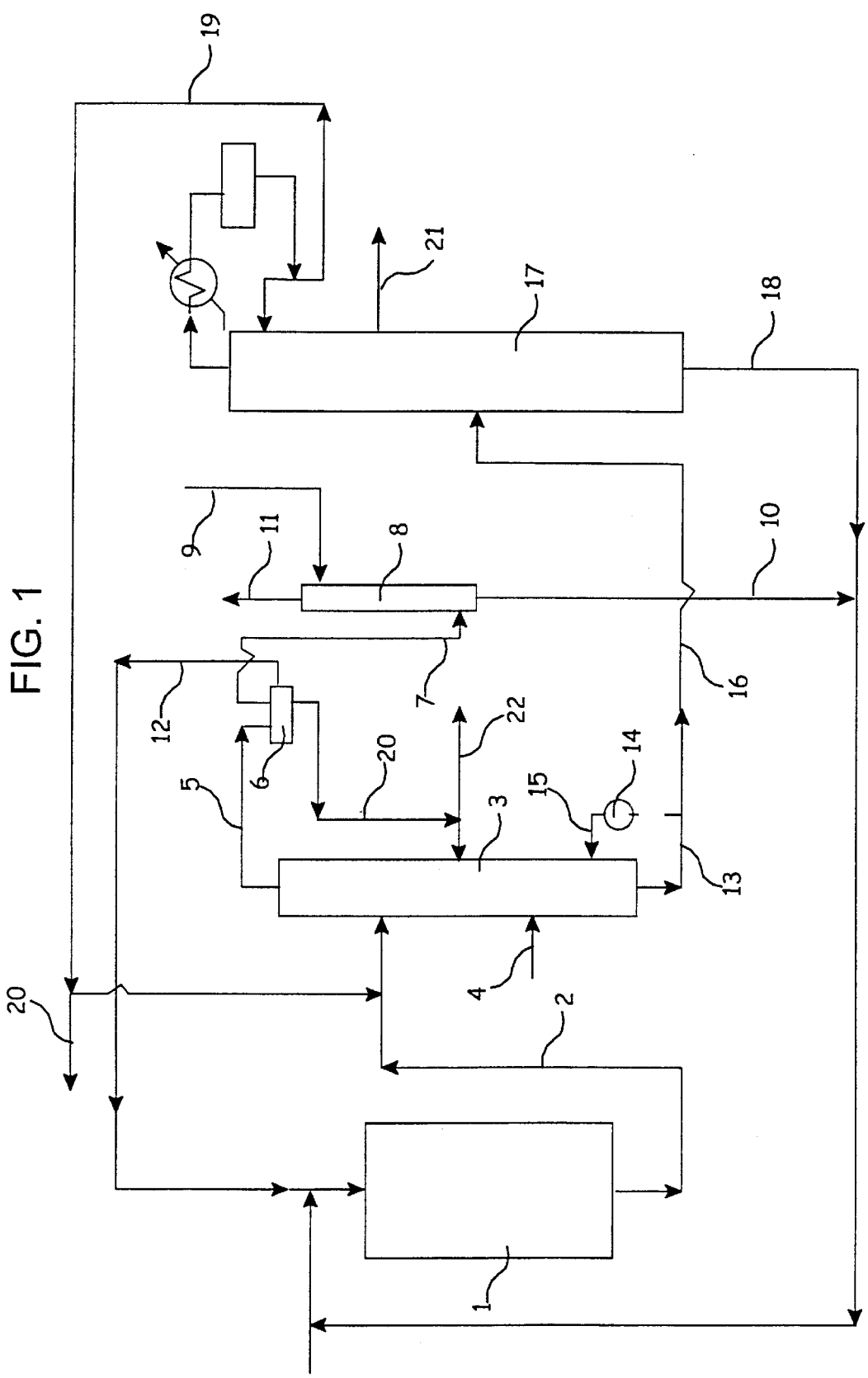
FIG. 1 illustrates schematically practice of the invention.

The invention can, perhaps, best be described with reference to the attached drawing in the context of the separation of minor amounts of di-ether and other impurities from DPTB.

Referring to the drawing, DPG and isobutylene are reacted in reactor 1 over an acid resin catalyst in accordance with conventional procedures to form DPTB. The reactor product mixture which is comprised of DPTB, unreacted isobutylene, unreacted DPG, and di-propylene glycol di-tert-butyl ether passes via line 2 to distillation column 3. Distillation column 3 represents a multi stage fractional distillation column. Introduced to column 3 at a point in the upper section via line 2 is the reaction product from reactor comprised mainly of DPG and di-propylene glycol mono-tert-butyl ether contaminated with small amounts of di-ether and usually containing unreacted isobutylene and some isobutylene oligomers such as diisobutylene. Introduced into column 3 via line 4 below the DPTB introduction point is a liquid water or a steam stripping component stream. Pressure in the column is regulated in order to maintain a temperature in the reboiler at a point which will not cause substantial degradation of the organic feed. The presence of water in the bottom also keeps temperature low even at a atmospheric pressure in the column. Generally it is advantageous to maintain conditions such that the reboiler temperature does not exceed about 175° C. A further important consideration is that sufficient heat is supplied to the column via the reboiler to ensure that the liquid water stripping component stream introduced via line 4 is completely vaporized in the distillation column. It is generally desirable to maintain a pressure of 50 mm Hg or more at the top of the column in order to provide for easy condensation of the stripping component with cooling tower water and to keep the reboiler at generally acceptable temperatures. More preferably, the column is maintained at a pressure above about 300 mm Hg.

Boil up of the product in the reboiler is maintained such that all the stripping component, as well as associated organic materials removed overhead are vaporized and the heat losses are accounted for. There is no external reflux of significance at the top of the column. While it is not desirable to provide reflux to the top of the column, this may be done for ease of operation.

Below the water stripping component introduction point in the column, heated organic product vapors rising from the reboiler strip the down coming organic materials and the stripping action is assisted by the stripping component present at the injection point and below. Above the stripping water injection point, stripping vapor rising through the column strips the down coming product removing both isobutylene and di-ether whose volatility relative to the product DPTB is enhanced by the water stripping vapor. Stripping component vapor along with various impurities and some DPTB are removed from the column via line 5 and condensed using tower water.

The overhead condensate is phase separated in separator 6 with uncondensed vapors mainly comprised of isobutylene passing via line 7 to scrubber 8 wherein it is scrubbed with feed DPG introduced via line 9. The DPG containing scrubbed isobutylene passes via line 10 to reactor 1. Light materials are flared via line 11. The di-propylene glycol di-tert-butyl ether rich organic layer is recycled via line 12 to reactor 1 where the DE reacts with DPG to form the desirable DPTB. This stream may be fully or partially withdrawn for disposal.

The aqueous phase rich in DPTB and DPG is returned to the column to supply the stripping water and to return the DPG and DPTB to the column thus minimizing their loss. A small purge of the aqueous phase is taken as needed.

The bottoms organic stream comprised mainly of DPTB and unreacted DPG is removed as liquid from column 3 via line 13 and most passes to reboiler 14 wherein the organic stream is heated and returned via line 15 to column 3 to provide the necessary distillation heat. The remaining portion is removed as product passing via line 16 to distillation column 17 wherein product DPTB is recovered by conventional distillation. Bottoms comprising unreacted DPG passes via line 18 back to reactor 1 or to the isobutylene scrubber 8.

Overhead lights are removed via line 19 and recycled to column 3, a purge being removed via line 20.

Product comprised of DPTB and DPG substantially free of di-ether is recovered via line 21.

Generally, make-up stripping component is used in amount of about 1–25% by weight based on the feed, preferably about 2–10 wt %. Recycle of the water phase from decanter 6 provides additional stripping water.

It is important that the feed to column 3 comprise DPG in order that impurities removal be accomplished. Amounts of DPG relative to DPTB fed of 5–200% by weight, preferably 50–100% by weight are generally suitable.

EXAMPLE 1

By way of illustration in a specific practice of the present invention a product stream mainly comprised of di-propylene glycol mono-tert-butyl ether is purified by the procedure of the present invention. A stream comprised of 48 wt % di-propylene glycol mono-tert-butyl ether and containing 3.8 wt % di-propylene glycol di-tert-butyl ether and 48% unreacted DPG is introduced into column 3 via line 2 at the rate of 100 ml per hr. Column 3 is a fractionation column containing 40 distillation trays. The organic stream introduced via line 2 enters the column at the top tray. Also introduced into column 3 via line 4 is a liquid water stream which is introduced at the rate of 200 ml per hr. and enters column 3 at tray 20.

Column 1 is maintained at an atmospheric pressure and overhead temperature of 99° C. Upon entering the column, the liquid water is immediately vaporized in the section in which it is introduced, the vaporization causing substantial internal condensation and reflux of the materials which are contained in the column. The di-propylene glycol mono-tert-butyl ether component flows downwardly through the column and is removed via line 13 with a portion passing to reboiler 14 and back to column 3 via line 15. Reboiler temperature is about 135° C. From the reboiler the heated stream is circulated via line 15 back to the bottom of column 3 thus providing organic stripping vapor in the lower section of column 3 and the heat needed to operate the distillation. A net purified product comprising substantially equal amounts of DPG and DPTB and some water and essentially free of DE is removed via line 16 together with water and DPG. This stream passes to column 17 wherein by conventional distillation DPTB is recovered essentially free of DE. The net product is recovered at the rate of 90 ml per hr.

In column 3, the vaporized water passing upwardly through the column strips from the downwardly flowing DPTB the impurities which were associated with the di-propylene glycol mono-tert-butyl ether feed stream and a vapor stream is removed overhead via line 5 at the rate of 95 ml per hr.

From the above description it can be seen that practice of the invention provides a unique and successful method for conveniently purifying organic streams such as the di-propylene glycol mono-tert-butyl ether from di-ether impurities without the necessity for the elaborate and extensive procedures which were used in the prior art, and without a significant loss of desirable product.

EXAMPLE 2

This example illustrates the removal of di-ethylene glycol di-ethyl ether (DEDE) from a blend of diethylene glycol (DEG), di-ethylene glycol mono-ethyl ether (DEME), and di-ethylene glycol di-ethyl ether.

A stream comprised of 72.5% DEG, 2.5% DEDE and 25% DEME at 280° F. is introduced to the top section of a distillation column with 40 stages of packing; at a rate of 1000 lbs/hr. Water at 212° F. is introduced to the bottom section of the column at a rate of 50 lb/hr. Bottoms temperature is maintained at 380° F. while the temperature at the top of the column is 336° F. An overhead vapor stream is taken from the top of the column to a condenser at a rate of 350 lbs/hr and, after condensation, the condensate is separated into two liquid phases. The lighter organic phase is withdrawn at a rate of 205 lbs/hr and contains 21% water, 12% DEDE and 67% DEME. The heavier, aqueous phase containing 60% water, 0.4% DEDE, 1.2% DEME and 38% DEG is returned to the bottom section of the column. Product is withdrawn from the bottom section at a rate of 845 lbs/hr and contains 86% DEG, 13% DEME and only a trace of DEDE. This stream, free of DEDE can be further purified by conventional distillation to separate pure DEME.

I claim:

1. A process for separating a glycol di-alkyl ether from a glycol mono-alkyl ether which comprises introducing a mixture of glycol di-alkyl either and glycol mono-alkyl ether to be separated into the upper section of a fractional distillation column and introducing a stream of liquid water or steam stripping component into said column, providing necessary vaporization by means of a bottoms reboiler, removing an overhead vapor stream comprised of the introduced stripping component together with at least a predominance of the glycol di-alkyl ether removing a liquid bottoms stream comprised of the glycol mono-alkyl ether reduced in the glycol di-alkyl ether, heating part of the bottoms to vaporize at least a portion thereof, and returning the heated bottoms to the column.

2. The process of claim 1 wherein said glycol di-alkyl ether is di-propylene glycol di-tert-butyl ether and said glycol mono-alkyl ether is di-propylene glycol mono-tert-butyl ether.

3. The process of claim 1 wherein said glycol di-alkyl ether is di-ethylene glycol di-ethyl ether and said glycol mono-alkyl ether is di-ethylene glycol mono-ethyl ether.

* * * * *